United States Patent
Kompella et al.

(10) Patent No.: US 10,870,650 B2
(45) Date of Patent: Dec. 22, 2020

(54) PROCESS FOR THE PREPARATION OF AMORPHOUS IDELALISIB

(71) Applicant: NATCO PHARMA LIMITED, Hyderabad (IN)

(72) Inventors: Amala Kompella, Hyderabad (IN); Sreenivas Rachakonda, Hyderabad (IN); Venugopala Krishna Gampa, Hyderabad (IN); Subhash Kusumba, Hyderabad (IN); Durga Prasad Konakanchi, Hyderabad (IN); Pulla Reddy Muddasani, Hyderabad (IN); Venkaiah Chowdary Nannapaneni, Hyderabad (IN)

(73) Assignee: NATCO PHARMA LIMITED, Hyderabad (IN)

( * ) Notice: Subject to any disclaimer, the term of this patent is extended or adjusted under 35 U.S.C. 154(b) by 0 days.

(21) Appl. No.: 16/607,914

(22) PCT Filed: Apr. 11, 2018

(86) PCT No.: PCT/IN2018/050206
§ 371 (c)(1),
(2) Date: Oct. 24, 2019

(87) PCT Pub. No.: WO2018/198131
PCT Pub. Date: Nov. 1, 2018

(65) Prior Publication Data

US 2020/0095249 A1    Mar. 26, 2020

(30) Foreign Application Priority Data

Apr. 24, 2017 (IN) .............................. 201741014391

(51) Int. Cl.
*C07D 473/34* (2006.01)

(52) U.S. Cl.
CPC .................................. *C07D 473/34* (2013.01)

(58) Field of Classification Search
CPC ..................................................... C07D 473/34
See application file for complete search history.

(56) References Cited

FOREIGN PATENT DOCUMENTS

| CN | 104876931 A | 9/2015 |
|---|---|---|
| WO | 2005/113556 A1 | 12/2005 |
| WO | 2013/134288 A1 | 9/2013 |
| WO | 2016/108206 A2 | 7/2016 |
| WO | 2016/147206 A1 | 9/2016 |

OTHER PUBLICATIONS

International Search Report issued in connection with corresponding International Application No. PCT/IN2018/050206 dated Jul. 24, 2018; 2 pages.

*Primary Examiner* — Paul V Ward
(74) *Attorney, Agent, or Firm* — Kilpatrick Townsend & Stockton LLP

(57) ABSTRACT

The present invention relates to a process for the preparation of stable and 5 pure amorphous form of Idelalisib. Further, the present process is simple, more economical, cost effective and efficient method of manufacturing that is suitable for industrial scale-up having a high degree of chromatographic purity.

17 Claims, 1 Drawing Sheet

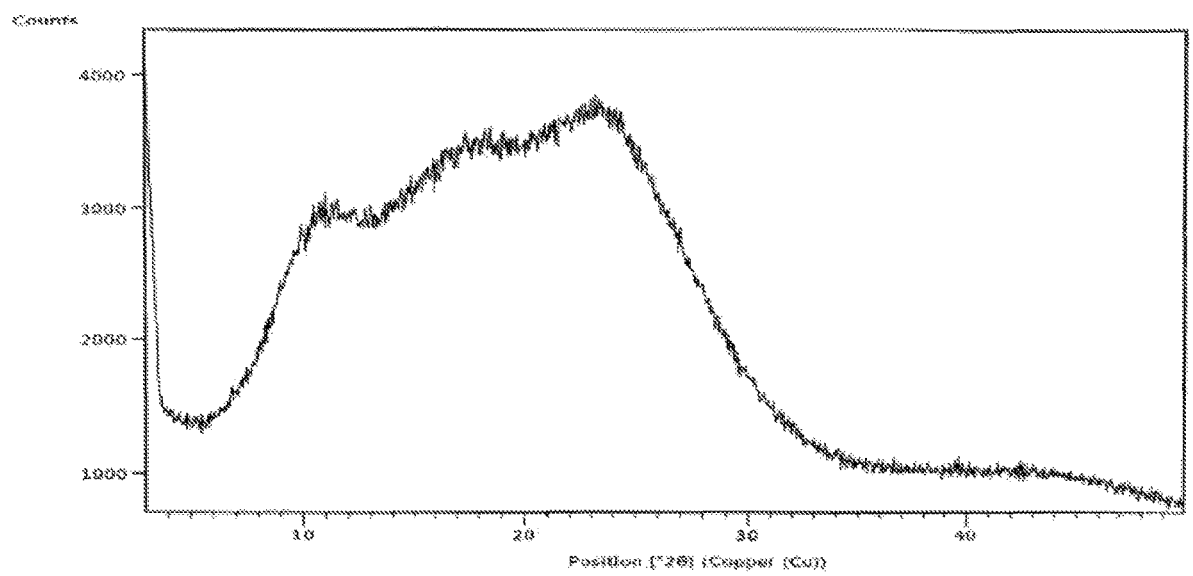

PROCESS FOR THE PREPARATION OF AMORPHOUS IDELALISIB

FIELD OF THE INVENTION

The present invention provide a process for the preparation of stable and pure amorphous Idelalisib.

BACKGROUND OF THE INVENTION

Idelalisib is (S)-2-(1-(9H-purin-6-ylamino)propyl)-5-fluoro-3-phenyl quinazolin-4(3H)-one having structural Formula I

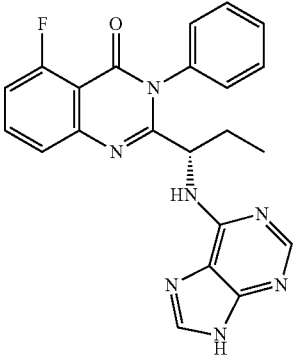

(I)

Idelalisib is an investigational, targeted, highly selective oral inhibitor of phosphoinositide 3-kinase (PI3K) delta, a protein that is critical for the activation, proliferation and survival of B lymphocytes.

International (PCT) Publication No. WO 2005/1 13556 A1 discloses preparation of Idelalisib and related compounds The process according to WO 2005/1 13556 A1 of Idelalisib, in which 2-fluoro-6-nitrobenzoic acid was reacted with oxalyl chloride in presence of catalytic amount of DMF, and the obtained acid chloride was reacted with aniline to form 2-fluoro-6-nitro-N-phenylbenzamide, the phenylbenzamide was reacted with N-Boc-L-2-aminobutyric acid in presence of thionyl chloride to form tert-butyl (S)-(1-(2-fluoro-6-nitro-N-phenylbenzamido)-1-oxobutan-2-yl)carbamate then the nitro carbamate was reduced using Zinc and acetic acid and the intermediate amino compound was cyclized and deprotected to give (S)-2-(1-aminopropyl)-5-fluoro-3-phenylquinazolin-4(3H)-one, finally the quinazolinone was reacted with 6-bromopurine to form Idelalisib. The crude product is purified by column chromatography, dissolved in ethanol and concentrated in vacuum to obtain Idelalisib but, does not discuss about its polymorphic form.

In addition, the process disclosed in WO 2005/1 13556 A1 ends up with low yield, less purity.

International (PCT) Publication No. WO 2013/134288 A1 discloses various crystalline polymorphic forms of Idelalisib, Form I, Form II, Form III, Form IV, Form V, Form VI and Form VII. Where Forms I and II are crystalline and anhydrous. Forms III to VII are solvates of iso-propyl alcohol (IPA), dimethylformamide (DMF), dimethylsulfoxide (DMSO), dichloromethane (DCM) and ethanol, respectively.

Therefore, there exists a need to develop a simple, more economical, cost effective and efficient method of manufacturing the Idelalisib that is suitable for industrial scale-up having a high degree of chromatographic purity.

SUMMARY OF THE INVENTION

In a first aspect of the present invention is to provide a process for the preparation of Idelalisib, comprising the steps of:

1) reacting the compound of formula-A with compound of formula-B in presence of a base in a solvent to obtain the compound of formula C;

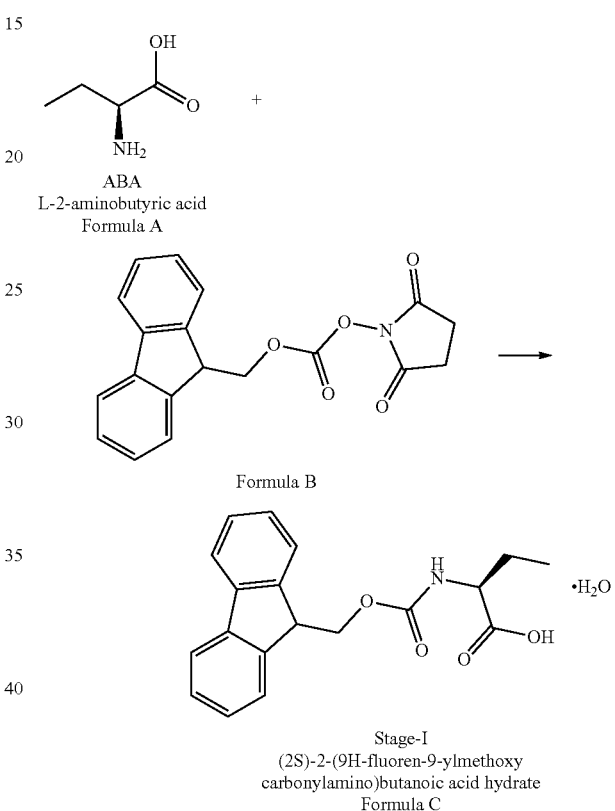

2) reacting the compound of formula-C with acid chloride in halogenated hydrocarbon solvent to obtain the compound of formula-D, which is treated with 2-amino-6-fluorobenzoic acid in polar aprotic solvent to obtain the compound of formula-E, which is further treated with Diphenylphosphine and pyridine in polar aprotic solvent to obtain the compound of formula-F,

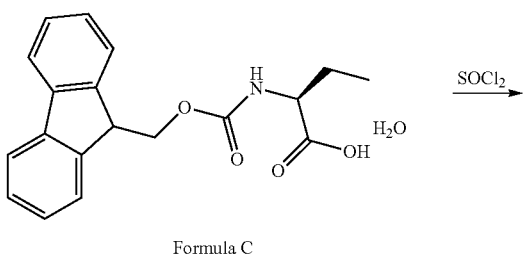

Formula C

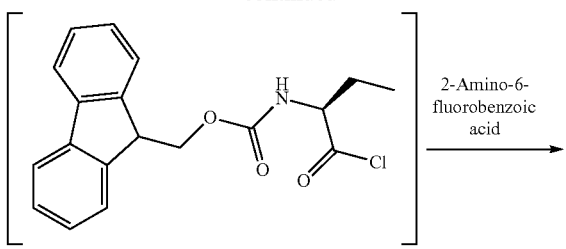

Formula D

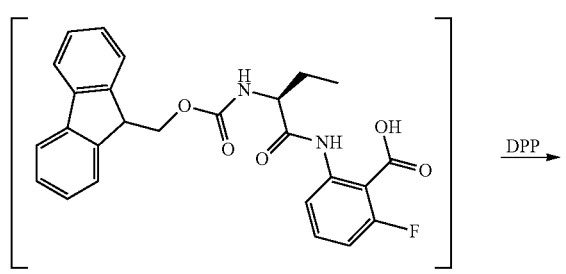

Formula E

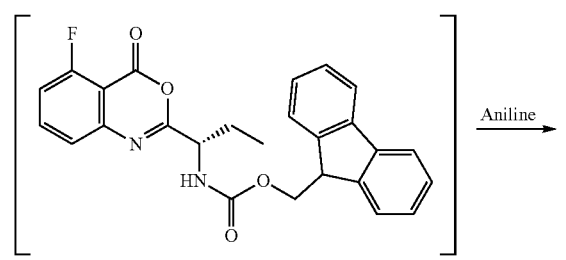

Formula F

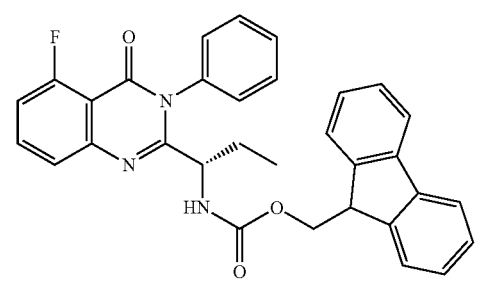

Formula G followed by treated with aniline to obtain the compound of formula-G.

3) deprotecting the compound of formula-G by treating with piperidine in polar aprotic solvent to obtain the compound of formula-H;

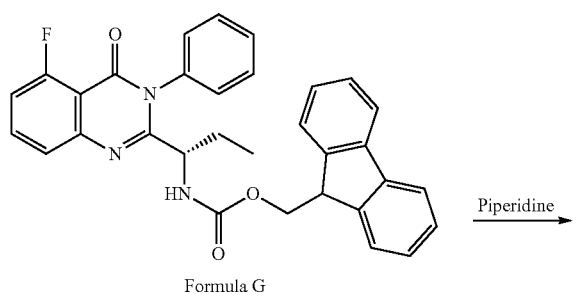

Formula G

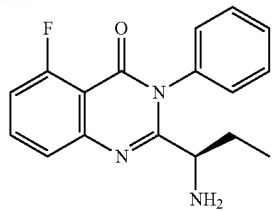

Formula H 4) reacting the compound of formula-H with 6-bromo-9H-purine in presence of a base in a suitable solvent, and then treating the obtained compound with an acid followed by base to provide Idelalisib.

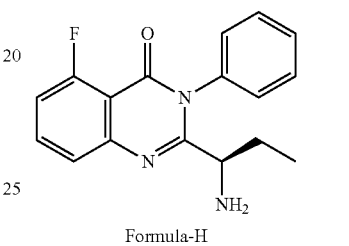

Formula-H

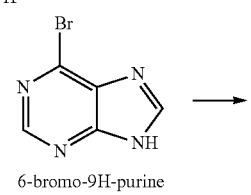

6-bromo-9H-purine

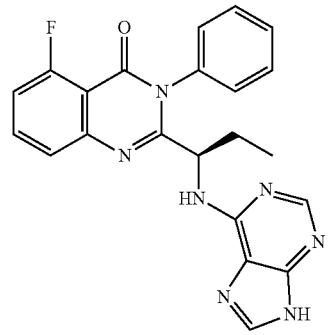

Idelalisib

In another aspect of the present invention is to provide a process for the purification of Idelalisib containing less than about 0.10% of 6-bromo purine, comprising the steps of:
1) dissolving the Idelalisib in halogenated hydrocarbon solvent,
2) treating the reaction mixture with ammonia solution and distilling off the solvent, and
3) isolating the pure Idelalisib by adding aqueous alcohol.

In another aspect of the present invention is to provide a process for the purification of Idelalisib containing the polar impurities less than about 0.15%, comprising the steps of:
1) dissolving the Idelalisib or Idelalisib solvate in aqueous alkyl sulfonic acid,
2) treating the reaction mixture with organic solvent,
3) separating the layers and adding chloro solvent to the aqueous layer,
4) neutralizing the obtained layer by adding the aqueous potassium carbonate, 5) distilling off the solvent from the reaction mixture, and
6) isolating the compound by adding aqueous alcohol.

In another aspect of the present invention is to provide a process for the preparation of amorphous Idelalisib, comprising the steps of:
1) dissolving the Idelalisib or Idelalisib solvate in alcoholic solvent,
2) heating the reaction mixture up to dissolution,
3) adding the reaction mixture of step-2) to polar solvent provides amorphous Idelalisib.

BRIEF DESCRIPTION OF THE DRAWINGS

FIG. 1: XRPD pattern of amorphous form of Idelalisib prepared according to example-5 or 7.

DETAILED DESCRIPTION OF THE INVENTION

The term "suitable solvent" used in the present invention refers to "hydrocarbon solvents" selected from aliphatic hydrocarbon solvents such as n-hexane, n-heptane, cyclohexane, petroleum ether and aromatic hydrocarbon solvents such as benzene, toluene, xylene and the like; "ether solvents" such as dimethyl ether, diisopropyl ether, diethyl ether, methyl tert-butyl ether, 1,2-dimethoxy ethane, tetrahydrofuran, 1,4-dioxane, monoglyme, diglyme and the like; "ester solvents" such as methyl acetate, ethyl acetate, isopropyl acetate, n-butyl acetate and the like; "polar-aprotic solvents such as dimethylacetamide, dimethylformamide, dimethylsulfoxide, N-methylpyrrolidone (NMP) and the like; "chloro solvents" such as dichloromethane/Methylene chloride, dichloroethane, chloroform, carbon tetrachloride and the like; "ketone solvents" such as acetone, methyl ethyl ketone, methyl isobutyl ketone and the like; "nitrile solvents" such as acetonitrile, propionitrile, isobutyronitrile and the like; "alcoholic solvents" such as methanol, ethanol, n-propanol, isopropanol, n-butanol, isobutanol, t-butanol and the like; "polar solvents" such as water or mixtures thereof.

As used herein the present invention the term "suitable base" refers to "alkali metal carbonates" such as sodium carbonate, potassium carbonate, lithium carbonate and the like; "alkali metal bicarbonates" such as sodium bicarbonate, potassium bicarbonate and the like; "alkali metal hydroxides" such as sodium hydroxide, potassium hydroxide, lithium hydroxide and the like; "alkali metal alkoxides" such as sodium methoxide, sodium ethoxide, potassium methoxide, potassium ethoxide, sodium tert.butoxide, potassium tert.butoxide, lithium tert.butoxide and the like; alkali metal hydrides such as sodium hydride, potassium hydride, lithium hydride and the like; alkali metal amides such as sodium amide, potassium amide, lithium amide and the like; and organic bases like dimethylamine, diethylamine, diisopropylamine, diisopropylethylamine, diisobutylamine, triethylamine, pyridine, 2-picoline, 3-picoline, 4-picoline, 4-dimethylaminopyridine (DMAP), N-methyl morpholine (NMM), 2,6-lutidine, lithium diisopropylamide; organosilicon bases such as lithium hexamethyldisilazide (LiHMDS), sodium hexamethyldisilazide (NaHMDS), potassium hexamethyldisilazide (KHMDS) or mixtures thereof.

In a first aspect of the present invention provides a process for the preparation of Idelalisib, comprising the steps of:
1) reacting the compound of formula-A with compound of formula-B in presence of base in a suitable solvent to obtain the compound of formula C,

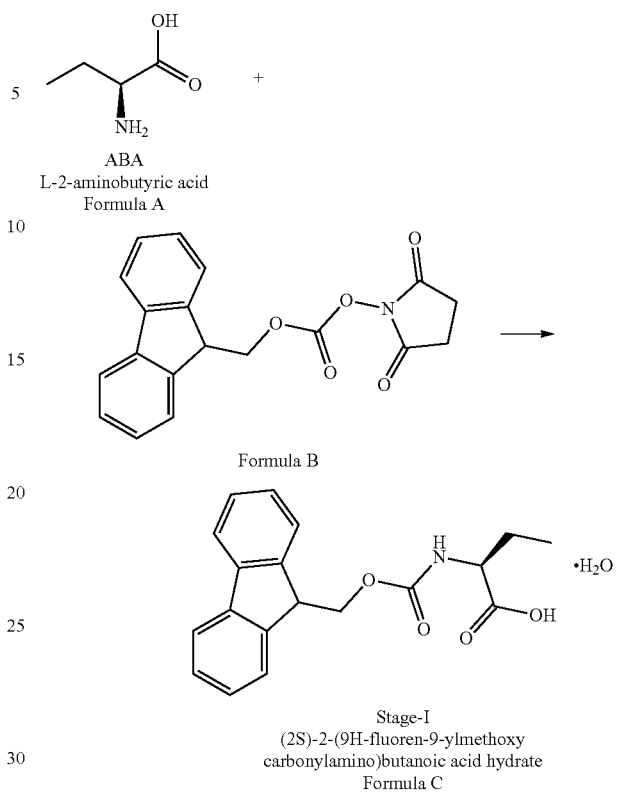

ABA
L-2-aminobutyric acid
Formula A

Formula B

Stage-I
(2S)-2-(9H-fluoren-9-ylmethoxy carbonylamino)butanoic acid hydrate
Formula C 2) reacting the compound of formula-C with acid chloride in halogenated hydrocarbon solvent to obtain the compound of formula-D, which is treated with 2-amino-6-fluorobenzoic acid in polar aprotic solvent to obtain the compound of formula-E, which is further treated with Diphenylphosphine and pyridine in polar aprotic solvent to obtain the compound of formula-F, followed by treated with aniline to obtain the compound of formula G,

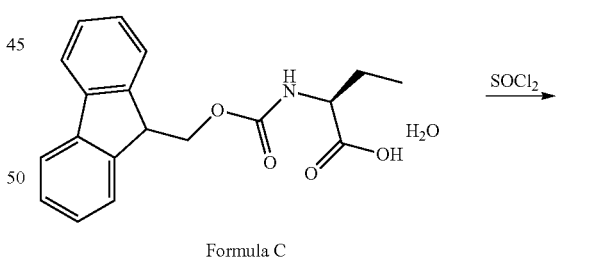

Formula C

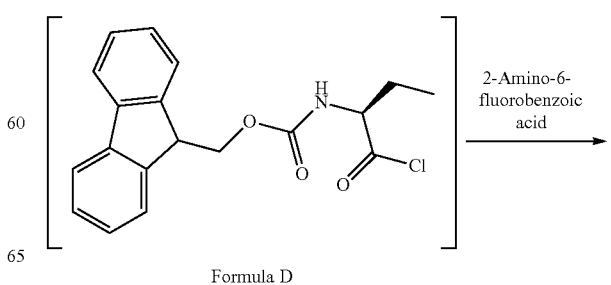

Formula D

-continued

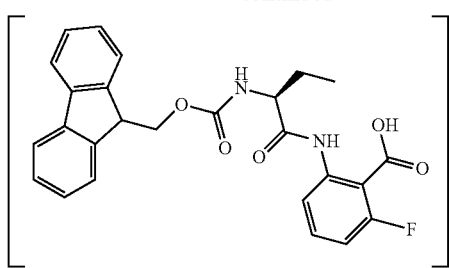

Formula E

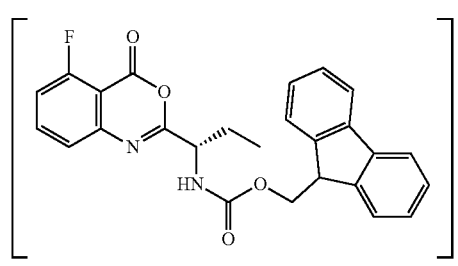

Formula F

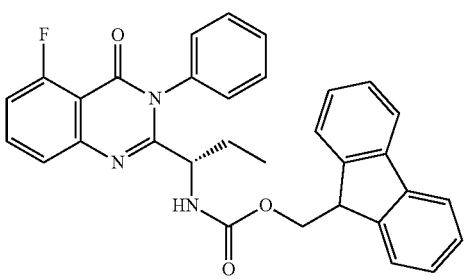

Formula G 3) deprotecting the compound of formula-G by treating with piperidine in polar aprotic solvent to obtain the compound of formula-H,

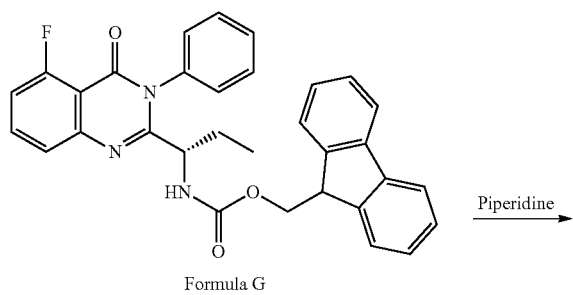

Formula H 4) reacting the compound of formula-H with 6-bromo-9H-purine in presence of a base in a suitable solvent, and then treating the obtained compound with an acid followed by base to provide Idelalisib.

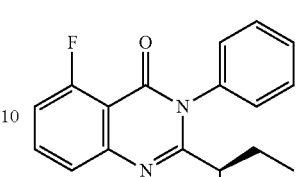

Formula H

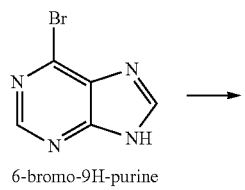

6-bromo-9H-purine

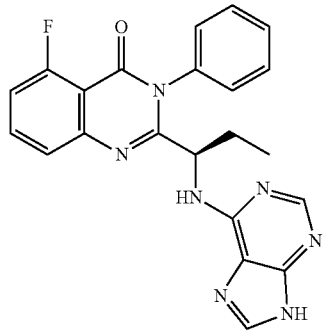

Idelalisib

Wherein, the base used in the step-(1) is selected from inorganic base such as carbonates selected from sodium carbonate, sodium bicarbonate, preferably sodium bicarbonate.

The acid chloride used in step-(2) is selected from the group consisting of thionyl chloride, phosphorus trichloride, phosphorus pentachloride and oxalyl chloride, preferably thionyl chloride.

The halogenated hydrocarbon solvent used in step-2 is selected form, methylene chloride, trichloroethane, tetrachloroethylene, preferably methylene chloride.

The polar solvent is used for preparation of compound of formula-E in step-(2) is selected from group comprising of dimethylformamide, 2-amino-2-methyl-1-propano, preferably dimethylformamide.

The polar solvent is used for preparation of compound of formula-F in step-(2) is selected from the group comprising of methanol, ethanol, isopropanol, preferably methanol.

The polar aprotic solvent used in step-(3) is selected from ester like ethyl acetate, isobutyl acetate, preferably ethyl acetate.

In a preferred embodiment of the present invention provides a process for the preparation of Idelalisib, comprising the steps of:

1) reacting the compound of formula-A with compound of formula-B in presence of sodium bicarbonate in tetrahydrofuran to obtain the compound of formula C,
2) reacting the compound of formula-C with thionylchloride in dichloromethane to obtain the compound of formula-D, which is treated with 2-amino-6-fluorobenzoic acid in dimethylformamide to obtain the compound of formula-E, which is further treated with Diphenylphosphine and pyridine in dimethylformamide to obtain the compound of formula-F, followed by treated with aniline to obtain the compound of formula G, 3) deprotecting the compound of formula-G by treating with piperidine in ethyl acetate to obtain the compound of formula-H, 4) reacting the compound of formula-H with 6-bromo-9H-purine in presence of N, N-Diisopropyl ethylamine in t-butanol, and then the obtained compound is treated with methanesulfonic acid in isopropyl alcohol followed by aqueous potassium carbonate solution provides Idelalisib.

In another aspect of the present invention provides a process for the purification of Idelalisib containing less than about 0.10% of 6-bromo purine, comprising the steps of:

1) dissolving the Idelalisib in halogenated hydrocarbon solvent,
2) treating the reaction mixture with ammonia solution and distilling off the solvent, and
3) isolating the pure Idelalisib by adding aqueous alcohol.

The Idelalisib or Idelalisib solvate used in step-(1) comprises the 6-bromo purine content about 20%.

The halogenated hydrocarbon solvent used in step-(1) is selected from methylene chloride, trichloroethane, tetrachloroethylene, preferably methylene chloride/dichloromethane.

The Idelalisib or Idelalisib solvate used in step-(1) is in form of crystalline, non-crystalline or solvate.

The aqueous alcohol solvent used in step-(3) is preferably isopropanol.

In a preferred embodiment of the present invention provides a process for the purification of Idelalisib containing less than about 0.10% of 6-bromo purine, comprising the steps of:

1) dissolving the Idelalisib in dichloromethane,
2) treating the reaction mixture with ammonia solution and distilling off the solvent, and
3) isolating the pure Idelalisib by adding aqueous isopropyl alcohol.

In another aspect of the present invention is to provide a process for the purification of Idelalisib containing the polar impurities less than about 0.15%, comprising the steps of:

1) dissolving the Idelalisib or Idelalisib solvate in aqueous alkyl sulfonic acid,
2) treating the reaction mixture with organic solvent,
3) separating the layers and adding chloro solvent to the aqueous layer,
4) neutralizing the obtained layer by adding the aqueous potassium carbonate,
5) distilling off the solvent from the reaction mixture, and
6) isolating the compound by adding aqueous alcohol.

The aqueous alkylsulfonic acid used in step-(1) is selected from p-toluenesulfonic acid, methane sulfonic acid, acetic acid, trifluromethane sulfonic acid preferably methane sulfonic acid.

The organic solvent is used in step-(2) is selected from polar aprotic solvent such as ester like ethyl acetate, isobutyl acetate; preferably ethyl acetate. The organic solvent used in step-(3) is selected from chloro solvent, preferably methylene chloride. And the aqueous alcohol solvent used in step-(6) is selected from methanol ethanol, isopropanol, preferably isopropanol.

In a preferred embodiment of the present invention provides a process for the purification of Idelalisib containing the polar impurities less than about 0.15%, comprising the steps of:

1) dissolving the Idelalisib or Idelalisib solvate in aqueous methanesulfonic acid,
2) treating the reaction mixture with ethyl acetate,
3) separating the layers and adding methylene chloride to the aqueous layer,
4) neutralizing the obtained layer by adding the aqueous potassium carbonate,
5) distilling off the solvent from the reaction mixture, and
6) isolating the compound by adding aqueous isopropanol.

In another aspect of the present invention is to provide a process for the preparation of amorphous Idelalisib, comprising the steps of:

1) dissolving the Idelalisib or Idelalisib solvate in alcohol solvent,
2) heating the reaction mixture up to dissolution,
3) adding the reaction mixture of step-(2) to polar solvent provides amorphous Idelalisib.

The Idelalisib or Idelalisib solvate used in step-1 is in form of crystalline, non-crystalline/amorphous or solvate.

The alcoholic solvent used in step-1 is selected from methanol, ethanol, isopropanol, preferably methanol and the polar solvent used in step-(3) is water.

In a preferred embodiment of the present invention is to provide a process for the preparation of amorphous Idelalisib, comprising the steps of:

1) dissolving the Idelalisib or Idelalisib solvate in methanol,
2) heating the reaction mixture up to dissolution,
3) adding the reaction mixture of step-(2) to water provides amorphous Idelalisib.

PXRD Method of Analysis:

PXRD analysis of Idelalisib compound of formula-I produced by the present invention were carried out using PANalytical X'pert PRO/DY-3248 X-Ray diffractometer using Cu Kα radiation of wavelength 1.5406° A with a step size of 0.026° and step time of 93.84 s.

The following examples are provided for illustration purpose only and are not intended to limit the scope of the invention.

Experimental Process

Example-1: (2S)-[[(9H-fluoren-9-ylmethoxy)carbonyl]amino]butanoic acid monohydrate)

The L-2-Aminobutyric acid (50.0 g) and $NaHCO_3$ (81.5 g) was dissolved in water (750 mL) at 20-25° C. Slowly Fmoc-OSu solution [171.7 g of FMOC-OSU was dissolved in 1050 ml of THF] was added to the reaction mixture and stir for 5 hour. After reaction completion the reaction mixture was acidified with diluted HCl up to pH<1.0 Filtered the obtained solid and dried.

The obtained crude compound was recrystallized with toluene and dried to get the title compound. Yield: 135 g; HPLC purity: 99.7%

Example-2: (2-[(1S)-1-[(9H-fluoren-9-ylmethoxy)carbonyl]aminopropyl]-5-fluoro-3-phenyl-4(3H)-quinazolinone)

The compound of example-1 (121.8 g) and thionyl chloride (126.6 g) was dissolved in dimethylformamide (0.5 mL) and methylene chloride (1.2 L) solvent mixture and heated for 2 hours. The solvent was distil to obtain the compound of formula D. Without isolating the compound of formula D was dissolved in pre cooled dimethylformamide (200 ml)

and added the solution of dimethylformamide (75 ml) contain 2-amino-6-fluoro-benzoic acid (50 g) at 0-10° C. Slowly rise the temperature up to 20 to 25° C. and stir for three hours. Observe the formation of compound of formula E, was reacted with pyridine (200 ml) and diphenyl phosphite (302.1 g) at 20 to 25° C. and stir for one hour. Observe the formation of compound of formula F, was treated with aniline (36 g) at 20-25° C. and stir for 3 hour to obtain the compound of formula G. Observed the complete formation of compound of formula G and added the methanol (1000 ml) to the reaction mixture. Adjust the pH of reaction mixture up to <1.0 with dilute HCl and added water (500 ml), stir for two hours. Filtered the obtained compound and leach with hot methanol to obtain the compound. Yield: 130 gm.

HPLC purity: 99.7%

Example-3: (2-[(1S)-1-aminopropyl]-5-fluoro-3-phenyl-4(3H)-quinazolinone)

The compound of example-2 (120 g, 0.23 moles) was dissolved in ethyl acetate and added piperidine (78.5 g) at 25 to 30° C. The reaction mixture was stir for about 12 hours at 25 to 30° C. The layers are separated and organic layer was washed with water and distilled the organic layer completely under reduced pressure. The obtained crude product was leached with hexane at 45 to 50° C. and dissolved in methylene chloride and subjected to charcoal treatment. The methylene chloride layer was distilled and recrystallized with toluene to obtain the compound.

Yield: 45 g.
HPLC purity: 99.7%

Example-4: (5-fluoro-3-phenyl-2-[(1S)-1-(9H-purin-6-ylamino) propyl]-4(3H)-quinazolinone) (Idelalisib)

The compound of example-3 (55 g, 0.18 moles) was dissolved in t-butanol and added 6-bromopurine (55 g, 0.27 moles) and N, N-Diisopropylethylamine (71.7 g, 0.55 mole). The reaction mixture was slowly heated up to reflux temperature and stir about 30 hours. After reaction completion distilled the solvent and formed residue was dissolved in methyl chloride. The Methylene chloride layer was washed successively with DM water and diluted ammonia. The layers are separated, the methylene chloride layer was subjected to charcoal treatment, followed by distillation. The formed crude product was isolated with 50% w/v aqueous isopropyl alcohol at 40 to 45° C. The obtained wet product was dissolved in aqueous methane sulfonic acid solution (16.36 g) and washed with ethyl acetate. Separated the aqueous and organic layers and methylene chloride was added to the aqueous layer. Further, the aqueous layer was neutralized with aqueous potassium carbonate solution and extracted into methylene chloride. The methylene chloride layer was washed with water and subjected to charcoal treatment. The methylene chloride was distilled completely under reduced pressure and isolated the product by adding 50% w/v aqueous isopropyl alcohol at 25 to 30° C. The wet product was dried at 60° C. to obtain compound as IPA solvate. Yield: 43.5 g HPLC purity: 99.88%

Example-5: Amorphous form of Idelalisib

The Idelalisib (30 g) was dissolved in methanol (300 mL) and subjected to carbon treatment. The methanol solution was added to the water (4.2 L) and stirred for 60 mints. The product is filtered and washed with water. Wet product was dried at 75° C. in vacuum tray to obtain the compound. Yield: 23 g HPLC Purity: 99.9%

The X-ray powder diffraction of obtained amorphous compound of formula-I is illustrated in FIG. 1.

Example-6: (5-fluoro-3-phenyl-2-[(1S)-1-(9H-purin-6-ylamino)propyl]-4(3H)-quinazolinone) (Idelalisib)

The compound of example-3 (75.0 g, 0.25 moles) was dissolved in t-butanol (1500 ml) and stirred for 15 minutes at 25 to 30° C. 6-bromopurine (75.3 g, 0.37 moles) and N, N-Diisopropylethylamine (98 g, 0.75 mole) were added to the reaction mixture and stirred for 15 minutes at the same temperature. The reaction mixture was slowly heated to 80-85° C. and stirred about 30 hours. Cooled the reaction mixture to 25 to 30° C. and distilled off the solvent under reduced pressure. Methylene chloride (1125 ml) followed by water were added to the reaction mixture and stirred for 30 minutes at 25 to 30° C. Separated both the organic and aqueous layers and the organic layer was washed successively with diluted ammonia solution and water. The organic layer was further treated with charcoal and distilled off the solvent under reduced pressure. The aqueous isopropyl alcohol (225 ml) was added to the obtained residue and raised the temperature to 40 to 45° C. and stirred the reaction mixture at the same temperature. Methanesulfonic acid (22.3 g, 0.2320) and ethylacetate (325 ml) were added to the obtained wet compound. Separated both the organic and aqueous layers followed by neutralizing the methylene chloride containing organic layer with aqueous potassium carbonate. Further, the methylene chloride layer was washed with water and subjected to charcoal treatment. The methylene chloride layer was distilled off under reduced pressure. The aqueous isopropyl alcohol (165 ml) was added to the obtained residue and raised the temperature to 40 to 45° C. and stirred the reaction mixture for 60 minutes at the same temperature. Cooled the reaction mixture to 25 to 30° C. and the wet product was dried to get the title compound. Yield: 58 g HPLC purity: 99.88%

Example-7: Amorphous form of Idelalisib

The Idelalisib (35 g) obtained from example-6 was dissolved in methanol (300 mL) and stirred the reaction mixture for 15 minutes at 25 to 30° C. Raised the temperature of the reaction mixture to 60 to 65° C. and stirred for 45 minutes at the same temperature. Cooled the reaction mixture to 25 to 30° C. and subjected to charcoal treatment. Filtered the obtained methanol layer and suck dried under reduced pressure. Further, the obtained filtrate was added to the water (2.45 L) and stirred for 60 minutes. Filtered the product, washed with water and dried to get the title compound. Yield: 28 g HPLC Purity: 99.9%

The X-ray powder diffraction of obtained amorphous compound of formula-I is illustrated in FIG. 1.

We claim:

1. A process for the preparation of the compound of Formula G:

(G) [structure]

the process comprising reacting the compound of Formula C:

(C) [structure] ·H₂O, with an acid chloride in a halogenated hydrocarbon solvent to obtain the compound of Formula D:

(D) [structure]

which is treated with 2-amino-6-fluoro-benzoic acid in a polar aprotic solvent to obtain the compound of Formula E:

(E) [structure]

which is further treated with diphenylphosphine and pyridine in a polar aprotic solvent to obtain the compound of Formula F:

(F) [structure]

followed by treatment with aniline to obtain the compound of Formula G.

2. The process according to claim 1, comprising reacting the compound of Formula C with thionyl chloride in dichloromethane to obtain the compound of Formula D, which is treated with 2-amino-6-fluoro-benzoic acid in dimethylformamide to obtain the compound of Formula E, which is further treated with diphenylphosphine and pyridine in dimethylformamide to obtain the compound of Formula F, followed by treatment with aniline to obtain the compound of formula G.

3. The process according to claim 1, wherein the process further comprises the steps of:
   1) obtaining the compound of Formula C by reacting the compound of Formula A:

(A) [structure]

with the compound of Formula B:

(B) [structure]

in the presence of a base in a solvent to obtain the compound of Formula C;
   3) deprotecting the compound of Formula G by treatment with piperidine in a polar aprotic solvent to obtain the compound of Formula H:

(H) [structure]

and
4) reacting the compound of Formula H with 6-bromo-9H-purine in the presence of a base in a suitable solvent, and then treating the obtained compound with an acid followed by base to provide idelalisib:

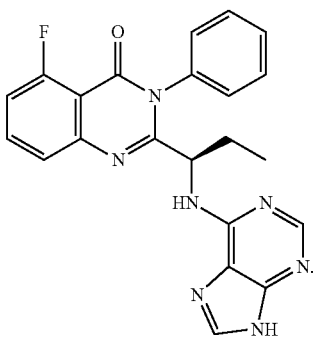 [SMILES: CC[C@@H](Nc1ncnc2[nH]cnc12)c1nc2cccc(F)c2c(=O)n1-c1ccccc1]

4. The process according to claim 3, wherein,
the acid chloride is selected from thionyl chloride, phosphorus trichloride, phosphorus pentachloride, and oxalyl chloride;
the halogenated hydrocarbon solvent is selected from methylene chloride, trichloroethane, and tetrachloroethylene;
the polar solvent used for preparation of the compound of Formula E is selected from dimethylformamide and 2-amino-2-methyl-1-propanol;
the polar solvent used for preparation of the compound of Formula F is selected from methanol, ethanol, and isopropanol;
in step 1, the base is an inorganic base; and
in step 3, the polar aprotic solvent is an ester.

5. The process according to claim 4, wherein the inorganic base in step 1 is a carbonate.

6. The process according to claim 5, wherein the carbonate is selected from sodium carbonate and sodium bicarbonate.

7. The process according to claim 4, wherein the ester in step 3 is selected from ethyl acetate and isobutyl acetate.

8. The process according to claim 3, comprising the steps of:
1) reacting the compound of Formula A with the compound of Formula B in the presence of sodium bicarbonate in tetrahydrofuran to obtain the compound of Formula C;
2) reacting the compound of Formula C with thionyl chloride in dichloromethane to obtain the compound of Formula D, which is treated with 2-amino-6-fluorobenzoic acid in dimethylformamide to obtain the compound of Formula E, which is further treated with diphenylphosphine and pyridine in dimethylformamide to obtain the compound of Formula F, followed by treatment with aniline to obtain the compound of Formula G;
3) deprotecting the compound of Formula G by treatment with piperidine in ethyl acetate to obtain the compound of Formula H; and
4) reacting the compound of Formula H with 6-bromo-9H-purine in the presence of N,N-diisopropylethylamine in t-butanol, and then treating the obtained compound with methanesulfonic acid in isopropyl alcohol followed by aqueous potassium carbonate solution to provide idelalisib.

9. Idelalisib obtained by the process according to claim 3, having a purity greater than 99.5% as determined by HPLC.

10. The process according to claim 3, wherein the process further comprises steps for the preparation of purified idelalisib, wherein:
the purified idelalisib contains less than about 0.10% of 6-bromopurine, and the process comprises:
i) dissolving the idelalisib obtained in step 4 in a halogenated hydrocarbon solvent,
ii) treating the reaction mixture with ammonia solution and distilling off the solvent, and
iii) isolating the pure idelalisib by adding an aqueous alcohol to the reaction mixture obtained in step ii; or
the purified idelalisib contains polar impurities in an amount less than about 0.15%, and the process comprises:
a) dissolving the idelalisib obtained in step 4 or a solvate thereof in an aqueous alkylsulfonic acid,
b) treating the reaction mixture with organic solvent,
c) separating the layers obtained in step b and adding a chloro solvent to the aqueous layer,
d) neutralizing the obtained layer by adding aqueous potassium carbonate,
e) distilling off the solvents from the reaction mixture, and
f) isolating the compound by an adding aqueous alcohol to the mixture obtained in step e.

11. The process according to claim 10, wherein the purified idelalisib contains less than about 0.10% of 6-bromopurine, and wherein the process comprises:
i) dissolving the idelalisib obtained in step 4 in dichloromethane,
ii) treating the reaction mixture with ammonia solution and distilling off the solvent, and
iii) isolating the pure idelalisib by adding aqueous isopropyl alcohol to the mixture obtained in step ii.

12. The process according to claim 10, wherein the purified idelalisib contains polar impurities in an amount less than about 0.15%, and wherein the process comprises:
in step a, the aqueous alkylsulfonic acid is selected from p-toluenesulfonic acid, methanesulfonic acid, acetic acid, and trifluromethanesulfonic acid;
in step b, the organic solvent is a polar aprotic solvent;
in step c, the organic solvent is a chloro solvent; and
in step f, the aqueous alcohol solvent is aqueous isopropyl alcohol.

13. The process according to claim 10, wherein the purified idelalisib contains polar impurities in an amount less than about 0.15%, and wherein the process comprises:
a) dissolving the idelalisib obtained in step 4 or a solvate thereof in aqueous methanesulfonic acid,
b) treating the reaction mixture with ethyl acetate,
c) separating the layers obtained in step b and adding methylene chloride to the aqueous layer,
d) neutralizing the obtained layer by adding aqueous potassium carbonate,
e) distilling off the solvent from the reaction mixture, and
f) isolating the compound by adding aqueous isopropyl alcohol to the mixture obtained in step e.

14. Idelalisib obtained by the process according to claim 10, having a purity greater than 99.5% as determined by HPLC.

15. The process according to claim 3, wherein the process further comprises steps for the preparation of amorphous idelalisib, which comprise the steps of:
i) dissolving the idelalisib obtained in step 4 or a solvate thereof in an alcohol solvent,
ii) heating the reaction mixture up to dissolution, and iii) adding the reaction mixture obtained in step ii to a polar solvent, thereby providing amorphous idelalisib.

16. The process according to claim 15, comprising the steps of:
i) dissolving the idelalisib obtained in step 4 or a solvate thereof in methanol,
ii) heating the reaction mixture up to dissolution, and
iii) adding the reaction mixture obtained in step ii to water, thereby providing amorphous idelalisib.

17. Idelalisib obtained by the process according to claim 15, having a purity greater than 99.5% as determined by HPLC.

\* \* \* \* \*